United States Patent
Smith (10) Patent No.: US 8,123,913 B2
(45) Date of Patent: Feb. 28, 2012

(54) PROCESS FOR SEPARATING DIISOPROPYLBENZENE (DIPB) AND TRIISOPROPLYBENZENE (TIPB) FROM A FEED COMPRISING DIPB, TIBP, AND POLYALKYLATE HEAVIES

(75) Inventor: Michael R. Smith, Rolling Meadows, IL (US)

(73) Assignee: UOP LLC, Des Plaines, IL (US)

( * ) Notice: Subject to any disclaimer, the term of this patent is extended or adjusted under 35 U.S.C. 154(b) by 1016 days.

(21) Appl. No.: 11/622,860

(22) Filed: Feb. 26, 2008

(65) Prior Publication Data

US 2009/0173615 A1  Jul. 9, 2009

(30) Foreign Application Priority Data

Jan. 9, 2008 (WO) .................. PCT/US08/50622

(51) Int. Cl.
 - *B01D 3/14* (2006.01)
 - *B01D 3/42* (2006.01)
 - *C07C 7/04* (2006.01)
 - *C07C 15/00* (2006.01)

(52) U.S. Cl. .............. 203/2; 203/4; 203/94; 203/98; 203/99; 203/DIG. 19; 585/804

(58) Field of Classification Search ............ 203/2, 4, 203/94, 98, 99, DIG. 19; 585/804
See application file for complete search history.

(56) References Cited

U.S. PATENT DOCUMENTS

| | | |
|---|---|---|
| 3,308,069 A | 3/1967 | Wadlinger et al. |
| 3,435,091 A | 3/1969 | Hofmann et al. |
| 3,437,615 A | 4/1969 | Hanson et al. |
| 3,518,165 A * | 6/1970 | Ward .................. 203/78 |
| 3,527,823 A | 9/1970 | Jones |
| 4,169,111 A | 9/1979 | Wight |
| 4,316,997 A | 2/1982 | Vaughan |
| 4,341,914 A | 7/1982 | Berger |
| 4,459,426 A | 7/1984 | Inwood et al. |
| 4,555,311 A | 11/1985 | Ward |
| 4,587,370 A | 5/1986 | DeGraff |
| 4,774,377 A | 9/1988 | Barger et al. |
| 4,798,816 A | 1/1989 | Ratcliffe et al. |
| 4,870,222 A | 9/1989 | Bakas et al. |
| 4,891,458 A | 1/1990 | Innes et al. |
| 5,003,119 A | 3/1991 | Sardina et al. |

(Continued)

FOREIGN PATENT DOCUMENTS

| EP | 0 272 830 B1 | 6/1988 |
|---|---|---|
| EP | 0 424 393 B1 | 5/1991 |

(Continued)

*Primary Examiner* — Virginia Manoharan
(74) *Attorney, Agent, or Firm* — Mark R Willis (57) ABSTRACT

Processes and apparatuses for separating diisopropylbenzene (DIPB) and triisopropylbenzene (TIPB) from a feed including DIPB, TIPB, and polyalkylate heavies are disclosed. The disclosed processes include introducing the feed into a distillation column having a column top pressure of less than 5 psia, a column bottoms pressure of less than 3 psi, and preferably 2 psi or less above the column top pressure with a bottoms temperature ranging from about 435° F. to about 465° F. The processes also include taking off a side draw including at least 99.8 wt % of the DIPB and at least 50 wt % of the TIPB present in the feed and a bottoms stream including at least 95 wt % of the heavies contained in the distillation feed. The low temperature bottoms temperature enables high pressure steam to be used as the bottoms reboiler heat source.

14 Claims, 6 Drawing Sheets

U.S. PATENT DOCUMENTS

| | | |
|---|---|---|
| 5,030,786 A | 7/1991 | Shamshoum et al. |
| 5,073,653 A | 12/1991 | Butler |
| 5,177,285 A | 1/1993 | Van Opdorp et al. |
| 5,196,623 A | 3/1993 | Butler |
| 5,256,392 A | 10/1993 | Shamshoum |
| 5,522,984 A | 6/1996 | Gajda et al. |
| 5,847,253 A | 12/1998 | Ho et al. |
| 5,980,859 A | 11/1999 | Gajda et al. |
| 5,998,684 A | 12/1999 | Ho et al. |
| 6,008,422 A | 12/1999 | Schulz et al. |
| 6,013,848 A | 1/2000 | Chen et al. |
| 6,084,125 A | 7/2000 | Kingsley et al. |
| 6,096,935 A | 8/2000 | Schulz et al. |
| 6,150,578 A | 11/2000 | Ho et al. |
| 6,339,179 B1 | 1/2002 | Schulz et al. |
| 6,392,114 B1 | 5/2002 | Shields et al. |
| 6,642,425 B2 | 11/2003 | Winder et al. |
| 6,710,003 B2 | 3/2004 | Jan et al. |
| 6,781,025 B2 | 8/2004 | Dandekar et al. |
| 7,267,746 B1 * | 9/2007 | Harris et al. .................. 202/160 |
| 2003/0028061 A1 * | 2/2003 | Weber et al. .................. 585/475 |
| 2004/0030211 A1 * | 2/2004 | Chi et al. ...................... 585/467 |
| 2005/0139517 A1 | 6/2005 | Waddick et al. |
| 2006/0211901 A1 | 9/2006 | Boyer et al. |

FOREIGN PATENT DOCUMENTS

| | | |
|---|---|---|
| EP | 0 439 632 A1 | 8/1991 |
| EP | 0 467 007 A1 | 1/1992 |
| EP | 0 467 007 B1 | 1/1992 |
| EP | 0 485 683 A1 | 5/1992 |
| JP | 58172327 | 10/1983 |
| JP | 4091039 | 3/1992 |
| JP | 4187647 | 7/1992 |
| WO | WO 89/10910 | 11/1989 |

* cited by examiner

PROCESS FOR SEPARATING DIISOPROPYLBENZENE (DIPB) AND TRIISOPROPLYBENZENE (TIPB) FROM A FEED COMPRISING DIPB, TIBP, AND POLYALKYLATE HEAVIES

BACKGROUND

1. Technical Field

This disclosure relates to processes for producing cumene More specifically, this disclosure relates to the recovery of polyalkylated benzene byproducts from the alkylation of benzene with propylene to form cumene, namely diisopropylbenzene (DIPB) triisopropylbenzene (TIPB), which can then be transalkylated back to cumene.

2. Description of the Related Art

The alkylation of aromatics with olefins to produce monoalkyl aromatics is a well developed art which is practiced commercially in large industrial units. One commercial application of this process is the alkylation of benzene with propylene to form cumene (isopropylbenzene) which is subsequently used in the production of phenol and acetone Those skilled in the art are therefore familiar with the general design and operation of such alkylation processes The performances of alkylation processes for producing monoalkyl aromatics such as cumene are influenced by the stability and activity of the solid catalyst at the operating conditions of the process. For example, as the molar ratio of aromatic (benzene) per olefin (propylene) increases, current catalysts typically exhibit an improved selectivity to the monoalkyl aromatic—cumene. But even at these high molar ratios of benzene per propylene, polyalkylbenzene by-products such as diisopropylbenzene (DIPB) and triisopropylbenzene (TIPB) will accompany cumene production.

Although the formation of DIPB and TIPB might be viewed as by-products that represent a reduction in the efficient use of the propylene, both DIPB and TIPB can be readily transalkylated with the benzene using a transalkylation catalyst to produce the more valuable cumene product. So-called combination processes combine a first alkylation process that produces primarily cumene but which also produces DIPB and small amounts of TIPB with a second transalkylation process that converts the DIPB and TIPB back to cumene in order to the maximize cumene production. Upstream of the second transalkylation, the DIPB and TIPB must be separated from the other heavy alkylation and transalkylation by-products such as diphenylalkanes, which are collectively referred to herein as "heavies."

The separation or recovery of DIPB and TIPB is performed in a "polyalkylate" column. Because currently utilized cumene operating conditions and catalyst systems produce mainly DIPB as byproduct, with very little TIPB, TIPB has not been economically worth recovering and the polyalkylate columns of cumene production areas are designed to recover DIPB, not TIPB. However, newer catalyst systems produce increased amounts of TIPB at optimum reaction conditions. As a result, there is a need for a process that efficiently recovers TIPB as well as DIPB.

However, there is a problem associated with the removal of TIPB from the heavies Current polyalkylate columns operate under vacuum at a top pressure of approximately 3 psia and at a bottom pressure of approximately 8-10 psia The most economical way to reboil at the bottom of the column is to use high-pressure steam. High-pressure steam is typically available at 600 psig and at 485° F. Unfortunately, current polyalkylate columns produce significant TIPB yield losses in the heavies stream or bottoms product.

Therefore, design changes to polyalkylate columns are needed to maintain or increase DIPB recovery and to significantly increase TIPB recovery. TIPB this can be accomplished, cumene yield can be increased using current transalkylation techniques

SUMMARY OF THE DISCLOSURE

In satisfaction of the aforenoted needs, a process for separating diisopropylbenzene (DIPB) and triisopropylbenzene (TIPB) from a feed comprising DIPB, TIPB, and polyalkylate heavies is disclosed. The disclosed process comprises: introducing the feed into a distillation column operating at a column top pressure of less than 5 psia, a column bottoms pressure of less than 3 psi above the column top pressure and a bottoms temperature ranging from about 435° F. to about 465° F.; and taking off a side draw comprising at least 99.8 wt % of the DIPB and at least 50 wt % of the TIPB present in the feed and a bottoms stream comprising at least 95 wt % of the heavies contained in the distillation feed.

In a refinement, the column operates at a bottoms pressure of about 2 psi above the column top pressure.

In a refinement, the bottoms temperature ranges from about 445° F. to about 450° F.

In a refinement, the side draw is taken off from the column at a side draw point or outlet. The column also has a number of theoretical stages X, wherein X is an integer that is greater than 40 and the uppermost stage is 1 and the lowermost stage is X. The side draw point is disposed at a stage below the uppermost stage integrally numbered from about 0 26·X to about 0 40·X from the uppermost stage Further, in this refinement, the feed point is disposed at a stage integrally numbered from about 0.31·X to about 0.62·X from the uppermost stage.

In a refinement, side draw comprises at least 99.9 wt % of the DIPB contained in the feed.

In a refinement, the side draw comprises at least 90 wt % of the TIPB contained in the distillation feed.

In a refinement, the process is conducted so as to produce hydrocarbon vapor at a top of the column and the process further comprises condensing at least a portion of the hydrocarbon vapor produced at the top of the column with a condenser. In a related refinement, the condenser is contained within the column. In another related refinement, the process further comprises converting at least some of the hydrocarbon vapor to hydrocarbon liquid, and taking off at least to some of the hydrocarbon liquid off the column as overhead drag prior to re-introducing another part of said hydrocarbon liquid into the column as reflux.

In another refinement, the condenser is a contact condenser disposed in the top of the column, and the process further comprises: converting at least some of the hydrocarbon vapor in the contact condenser to hydrocarbon liquid; taking off at least to some of the hydrocarbon liquid off the column at a side draw point disposed below the contact condenser; and passing at least some of hydrocarbon liquid taken off the column at the side draw point through a cooler prior to being re-introduced into the column through the contact condenser. In another related refinement, the process further comprises purging at least a portion of the hydrocarbon liquid as overhead drag prior to reaching the contact condenser, and recycling at least a portion of the hydrocarbon liquid to the column at a point below the contact condenser.

In another refinement, the condensing is conducted in a contact condenser disposed outside of the column, and the process further comprises: converting at least some of the hydrocarbon vapor to hydrocarbon liquid in the contact condenser; removing at least to some of the hydrocarbon liquid from the contact condenser; and passing at least some of hydrocarbon liquid removed from the contact condenser through a cooler prior to reintroducing the cooled hydrocarbon liquid into the contact condenser In a related refinement, the process further comprises purging a portion of the hydrocarbon liquid as overhead drag prior to being reintroduced into the contact condenser, and recycling a portion of the hydrocarbon liquid to the column after passing the hydrocarbon liquid through the contact condenser.

In another refinement, the condensing is conducted at a condenser top pressure and a condenser bottoms pressure that is less than about 0.5 psi above the condenser top pressure.

In another refinement, the process further comprises withdrawing a draw off from the distillation column at a draw off point below the side draw point, and at least a portion of the draw off is reboiled and then returned to the distillation column In another refinement, the bottoms temperature preferably ranges from about 440° F. to about 460° F.; more preferably, the bottoms temperature ranges from about 445° F. to about 455° F.

A process for producing cumene is also disclosed which comprises: concurrently passing benzene and propylene to an alkylation zone containing solid alkylation catalyst and operating under alkylation conditions to produce a first effluent comprising cumene, benzene, diisopropylbenzene (DIPB), triisopropylbenzene (TIPB), and heavies; separating the benzene as a first overhead from the first effluent to provide a first bottoms stream comprising cumene, DIPB, TIPB, and heavies; separating most of the cumene from the first bottoms stream to provide a second overhead comprising cumene and a second bottoms stream comprising DIPB, TIPB, and heavies; separating the DIPB and TIPB from the heavies in the second bottoms stream in a distillation column operating at a column top pressure of less than 5 psia and a column bottoms pressure less than 3 psi above the column top pressure and a bottoms temperature ranging from about 435 to about 465° F. so as to provide a side draw comprising at least 99.8 wt % of the DIPB and at least 50 wt % of the TIPB contained in the second bottoms stream and a third bottoms stream comprising at least 95 wt % of the heavies contained in the second bottoms stream; and passing the DIPB and TIPB contained in the side draw to a transalkylation zone An apparatus for the alkylation of benzene with propylene is also disclosed which comprises: a distillation column having a feed inlet in fluid communication with a feed stream comprising DIPB, TIPB, and heavies (and, optionally, small amounts of cumene); the column further comprising a top stream outlet, a bottoms stream outlet, and a side draw outlet; the distillation column having a control system to limit a column top pressure to less than 5 psia, a column bottoms pressure to less than about 3 psi above the column top pressure and a bottoms temperature ranging from about 435 to about 465° F. resulting in a side draw comprising at least 99.8 wt % of the DIPB and at least 50 wt % of the TIPB present in the feed and the bottoms stream comprising at least 95 wt % of the heavies contained in the distillation feed; the column having a number of theoretical stages X, wherein X is an integer that is greater than 40 and an uppermost stage is 1 and a lowermost stage is X, the side draw outlet being disposed at a stage integrally numbered from about 0.26·X to about 0 40·X from the uppermost stage and the feed inlet being disposed at a stage integrally numbered from about 0.31·X to about 0.62·X from the top from the uppermost stage.

Other advantages and features will be apparent from the following detailed description when read in conjunction with the attached drawings.

BRIEF DESCRIPTION OF THE DRAWINGS

For a more complete understanding of the disclosed methods and apparatuses, reference should be made to the embodiment illustrated in greater detail on the accompanying drawings, wherein.

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein

DETAILED DESCRIPTION OF THE PRESENTLY PREFERRED EMBODIMENTS

Figure 1:
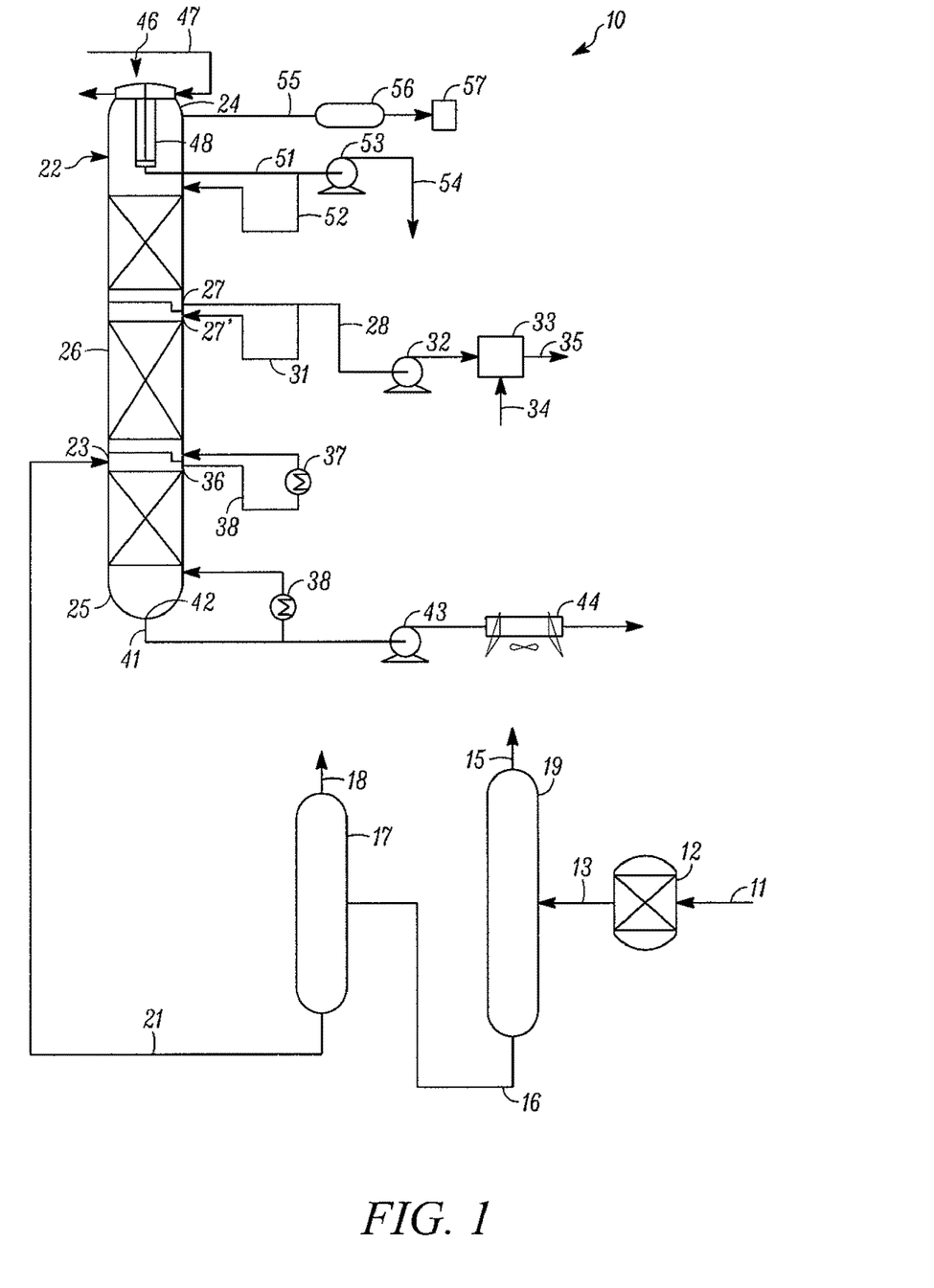
FIG. 1 is a process flow diagram of one disclosed process for separating DIPB and TIPB from a feed steam comprising DIPB, TIPB and polyalkylate heavies that includes an internal stab-in condenser.

Turning first to FIG. 1, a process 10 for producing cumene includes a benzene/propylene feed 11 that is passed through an alkylation zone 12 with a solid alkylation catalyst and which operates under alkylation conditions to produce an effluent stream 13 that contains cumene, benzene, DIPB, TIPB and heavies.

Details of possible alkylation catalysts will not be described here but preferred alkylation catalysts and a stacked catalyst system are described in co-pending and commonly assigned U.S. application Ser. Nos. 11/622,941, "Aromatic Transalkylation Using A Modified Y-85 Zeolite"), Ser. No. 11/622,925, "Aromatic Transalkylation Using A Modified LZ-210 Zeolite"), Ser. No. 11/622,896, "Modified Y-85 And LZ-210 Zeolites"), and 11/622,937, "Dual Zone Aromatic Alkylation Process"), which are incorporated herein by reference The first effluent stream 13 is then introduced to a column 14 which separates at least some of the benzene as an overhead stream 15 and which provides a bottom stream 16 that includes cumene, DIPB, TIPB and heavies, and which becomes a feed stream for the column 17 that separates the cumene as an overhead stream 18 and that produces a bottoms stream 21 which becomes a feed stream 21 for the polyalkylate column 22.

The feed 21 is introduced into the polyalkylate column 22 at an inlet port or feed point shown at 23. The column 22 includes a top 24, a bottom 25 and a cylindrical sidewall 26 with a plurality of the inlet and outlet ports disposed therein. A side draw outlet or side draw point is shown at 27 for withdrawing a recovery stream 28 of DIPB and TIPB A portion of the recovery stream 28 is recycled through the line 31 and fed back into the column 22 at the injection point 27'. The remaining portion of the recovery stream 28 and passes through the pump 32 and is sent to a transalkylation zone 33 where the DIPB and TIPB of the stream 28 is combined with a benzene feed 34 to produce a product stream 35 that is rich in cumene.

The outlet shown 36 is connected to the optional intermediate reboiler 37 by way of the reboiler line 38. The intermediate reboiler 37, if employed and depending upon the stage where the outlet 36 is located, may utilize stream at a medium pressure and temperature level (150-200 psig and 367-388° F.). Another option would be to employ a low flow rate of the high-pressure stream (600 psig, 489° F.) that may also be used as a heat source for the bottoms stream reboiler 38. The intermediate reboiler 37, if utilized, may use medium pressure stream as a heat source, which can be readily available as excess in some plants. The intermediate reboiler 37 may also contribute to the overall reduction in column pressure drop.

The bottoms stream or heavies stream 41 exits the bottom 25 of the column 22 through the outlet 42 Part of the heavies stream 41 is recycled through the reboiler 38 and the remaining portion of the bottoms stream 41 passes through the pump 43 and possibly a cooling apparatus 44 before it is used as a heavy alkylate feed elsewhere. One aspect of the disclosed process is that the temperature at the bottom 25 of the column 22 is relatively low, from about 435 to about 460° F., more preferably from about 445 to about 455° F. By using and exploiting the low bottoms temperature, conventional high-pressure stream (600 psig, 489° F.) may be used as a heat source for the bottoms reboiler 38 thereby reducing costs.

A stab-in condenser 46 is disposed inside the top 24 of the column 22. The condenser 46 includes a coolant flow line 47 and a condensing area 48 connected to an outlet line 51. The outlet line 51 is connected to a recycle line 52 which reenters the column 22 as reflux. Another portion of the flow through the outlet line 51 passes through the pump 53 and is removed through the line 54 as overhead drag Another top outlet line 55 is connected to a receiver 56 and a vacuum system 57. Because of the moderate pressure at the top 24 of the column 22 of less than 5 psia, and closer to 3 psia as illustrated in Tables 1 and 2 below, the vacuum system 57 may be a liquid ring vacuum system, a stream ejector vacuum system or a hybrid combination of the two. A single-stage liquid ring vacuum system is preferred due to the low cost.

Figure 2:
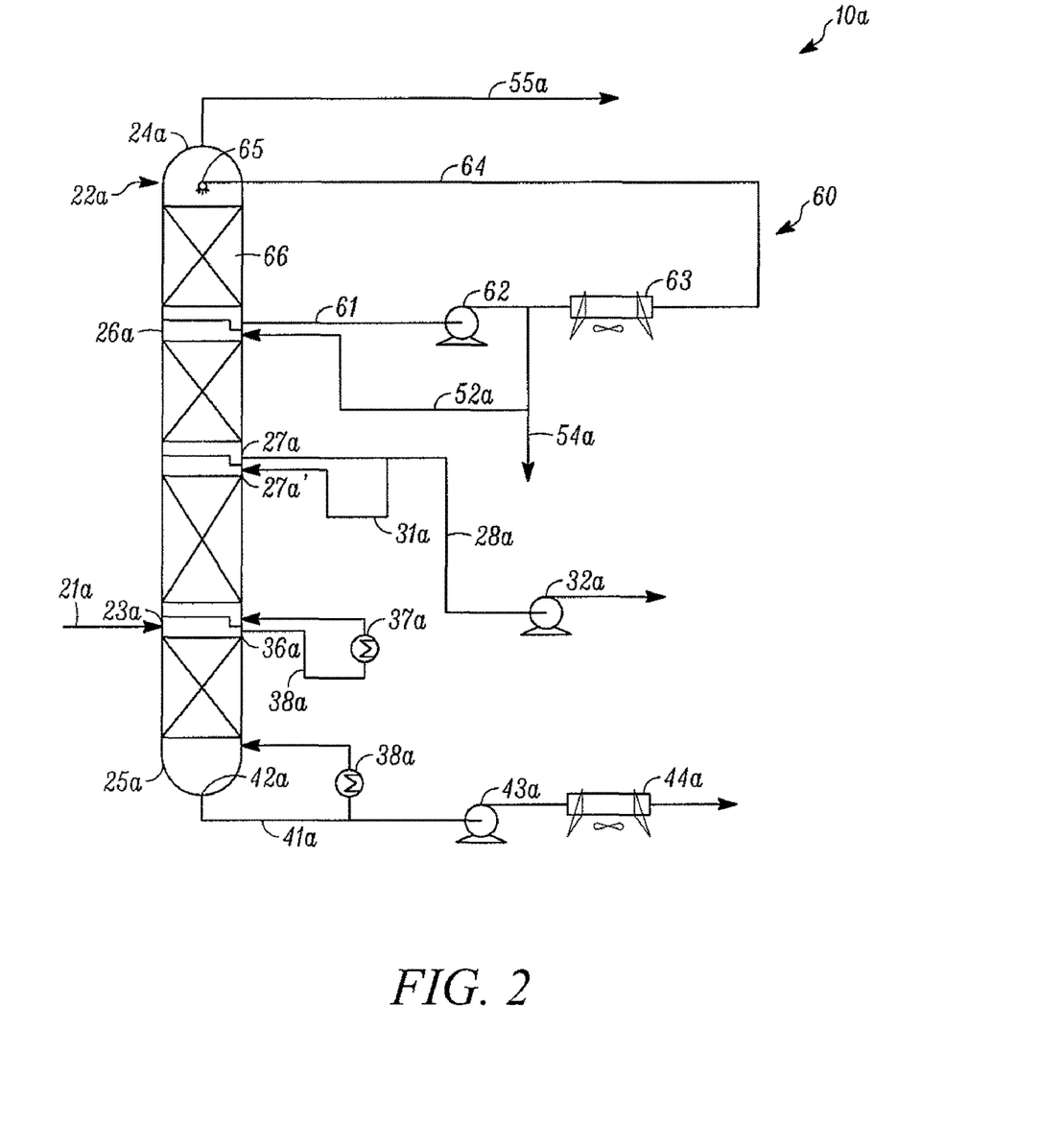
FIG. 2 is a process flow diagram of another disclosed process for separating DIPB and TIPB from a feed steam comprising DIPB, TIPB and polyalkylate heavies that includes an internal contact condenser.

The column 22 may include high-efficiency, random packing, disposed primarily above the feed inlet 23. Such packing is useful in reducing the overall column pressure drop from a typical 5-7 psi to a much lower pressure drop of 3 psi or less. That is, if the pressure at the at the top 24 of the column 22 is maintained at or about 3 psia or less, the pressure at the bottom 25 of the column 22 is maintained at or about 6 psia or less. Again, additional examples are provided in Tables 1 and 2 below FIG. 2 is a schematic diagram of an analogous process 10a that includes many of the same components shown in FIG. 1 except that the condenser is a contact condenser 60 which draws fluid out through a line 61 that is linked to a pump 62 before the fluid is passed through a cooler 63. A portion of the output from the pump 62 is recycled back to the column 22a through the line 52a and another portion is removed through the line 54a as overhead drag After the fluid drawn from the column through the line 61 and cooled in the cooler 63, the liquid returns to the column 22a through the line 64 and liquid distribution device or nozzle 65 that is directed downward so the downwardly directed cooled liquid makes intimate contact with the vapors that are traveling upwardly through the vessel section 66 disposed within an upper portion of the column 22a. The vessel section 66 may be open or filled with packing or similar vapor-liquid contacting materials or devices. The overhead is removed through a line 55a which is also connected to a receiver and vacuum system (not shown in FIG. 2; see FIG. 1). The remaining elements of FIG. 2 that are the same or similar to those shown in FIG. 1 have been numbered accordingly with the suffix "a" and a detailed discussion will not be repeated here.

Figure 3:
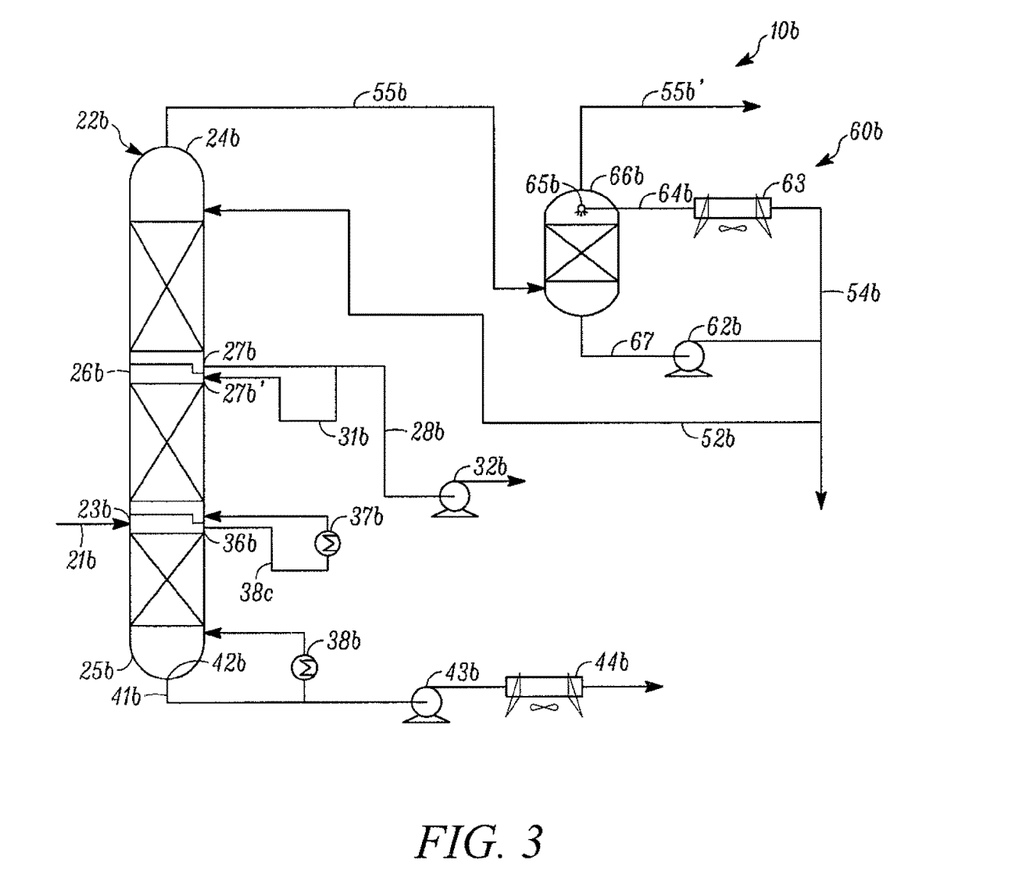
FIG. 3 is a process flow diagram of one disclosed process for separating TIPB and DIPB from a feed steam comprising TIPB, DIPB and polyalkylate heavies that includes an external contact condenser.

Similarly, FIG. 3 shows another analogous system 10b that includes an external contact condenser 60b as opposed to the "internal" contact condenser of FIG. 2. In FIG. 3, an overhead line 55b is connected to a vessel 66b The overhead vapors from the line 55b are exposed to downwardly traveling liquid within the vessel 66b that is emitted by the liquid distribution device 65b A bottoms stream 67 is taken off of the vessel 66b and passed through the pump 62b before the part of the bottoms stream 67 is passed to the cooler 63b and back to the vessel 66b via the line 64b through the liquid distribution device 65b and another part of the bottoms stream 67 is returned to the column 22b through the return line 52b An overhead drag may be removed through the line 54b. The vessel 66b may be open or filled with packing or similar vapor-liquid contacting materials or devices A second overhead line 55b' is connected to the vacuum system (not shown in FIG. 3, see FIG. 1; see also FIG. 1 for the upstream process components 11-18)

Like the contact stab-in condenser 46 of FIG. 1, the contact condensers 60, 60b also enable the systems 10a, 10b to have a low column pressure drop of less than 3 psi to lower than 2 psi and even down to the range of 0.5 psi.

Figure 4:
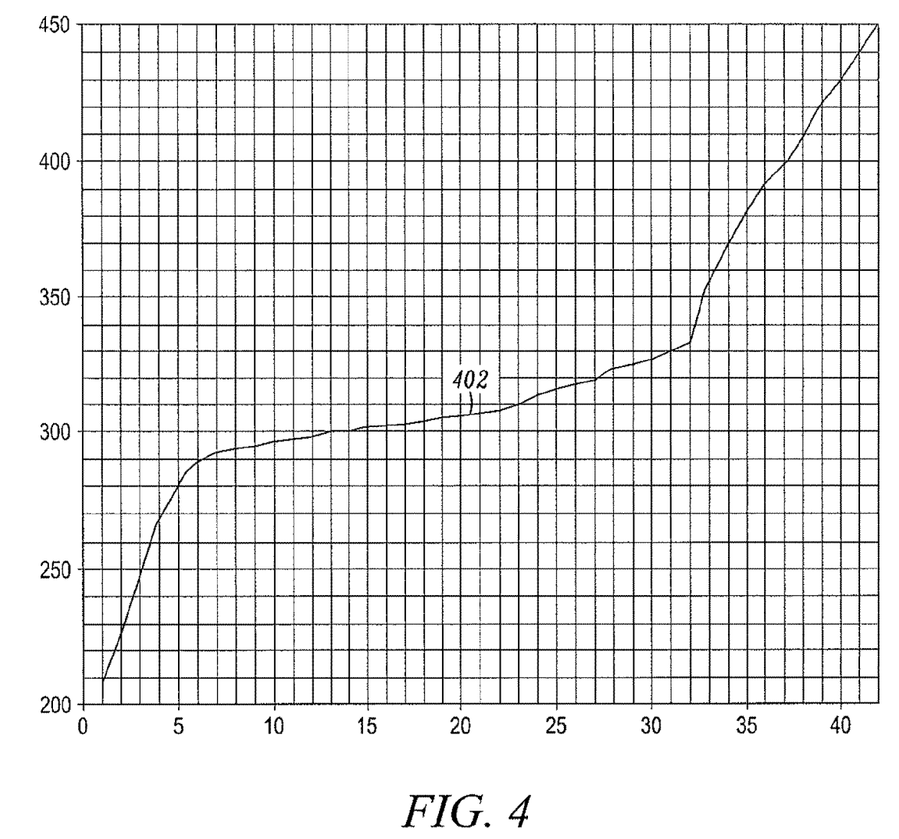
FIG. 4 illustrates, graphically, the number of theoretical stages (x-axis) versus temperature (y-axis) for a polyisopropylbenzene (PIPB) column with a receiver pressure of 2 5 psia, a 2 psi pressure drop from the top (overhead, 3 psia) to the bottom (5 psia) and a bottoms temperature of 450° F.

In FIG. 4, the number of theoretical stages (x-axis) versus temperature (y-axis) is shown as line 402 for a polyisopropylbenzene (PIPB) column 22, 22a, 22b with the pressure in the receiver 56 (see FIG. 1) at 2 5 psia, a 2 psi pressure drop from the top 24, 24a, 24b (overhead, 3 psia) to the bottom 25, 25a, 25b (5 psia) and a bottoms temperature of 450° F. As can be seen from FIG. 4, the number of theoretical stages for a PIPB column with a bottoms temperature of about 450° F. is about 42 The data in FIG. 4, like those in FIGS. 5 and 6 below, are based on engineering calculations, scientific distillation predictions, and experience with operating similar processes.

Figure 5:
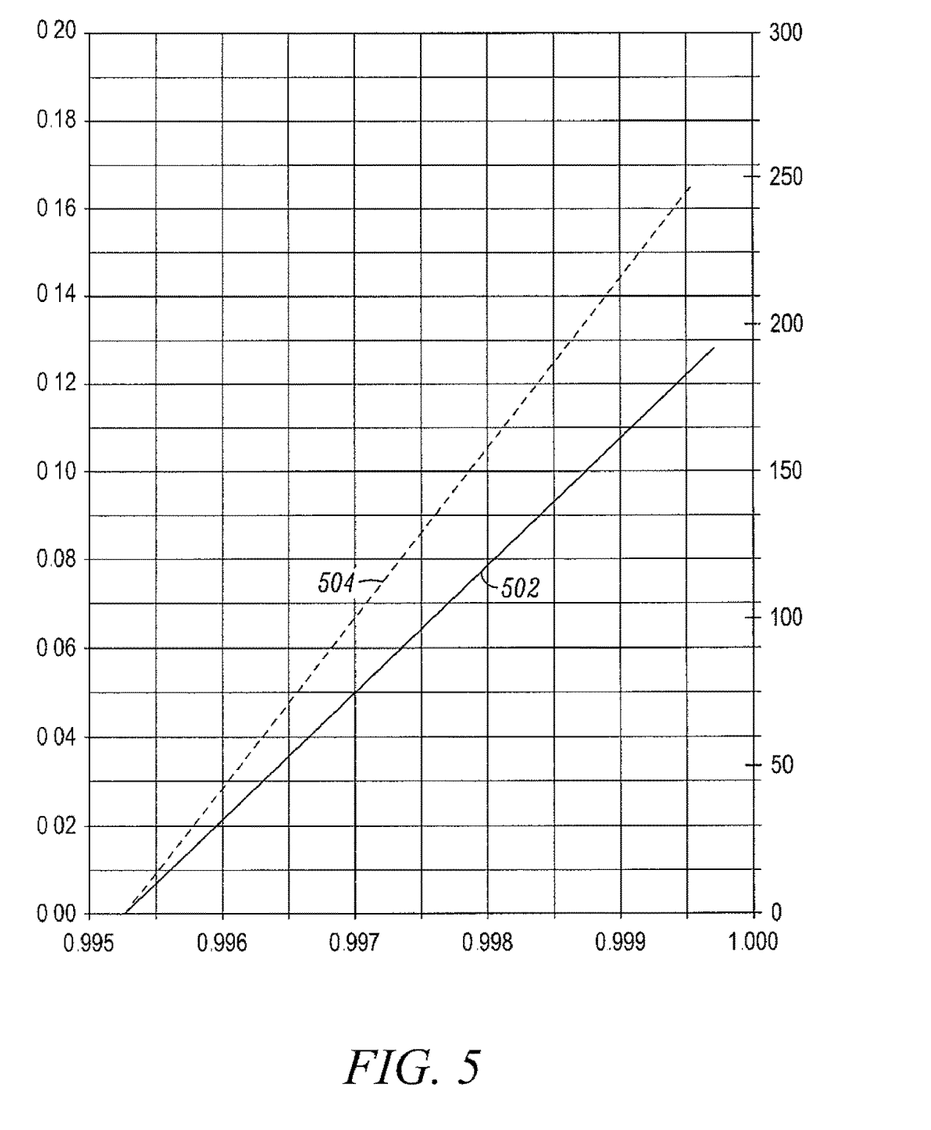
FIG. 5 illustrates, graphically, the effect of increasing PIPB recovery in a PIPB column on cumene yield for a world class capacity cumene process where incremental cumene yield (wt %) is plotted along the left y-axis, fractional DIPB recovery is plotted along the x-axis and incremental DIPB recovered (tonne/yr) is plotted along the right y-axis.
Figure 6:
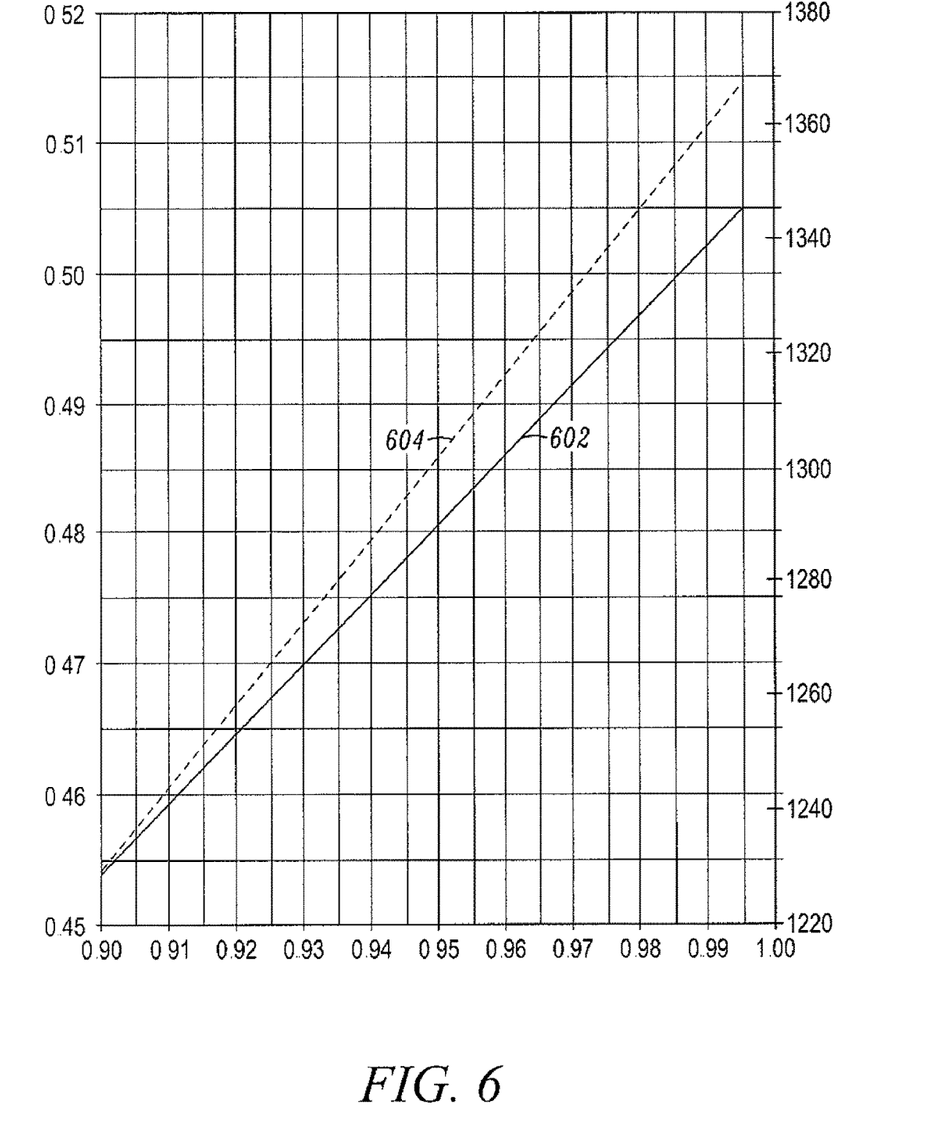
FIG. 6 illustrates, graphically, the effect of increasing TIPB recovery in a PIPB column on cumene yield for a world class capacity cumene process where incremental cumene yield (wt %) is plotted along the left y-axis, fractional TIPB recovery is plotted along the x-axis and incremental TIPB recovered (tonne/yr) is plotted along the fight y-axis.

The benefits of the disclosed processes and columns are illustrated graphically and FIGS. 5 and 6 In FIG. 5, the effect of increasing DIPB recovery in a PIPB column on cumene yield for a world class capacity cumene process is illustrated The line 502 represents the incremental cumene yield (left y-axis) versus fractional DIPB recovery (x-axis) and the line 504 represents incremental DIPB recovered (right y-axis) in tonne/yr versus fractional DIPB recovery (x-axis) As seen in FIG. 5, the cumene yield is increased by 0 12% when the DIPB recovery is increased from the conventional 99.5% to the 99.95%, which can significantly increase profit margin.

In FIG. 6, the effect of increasing TIPB recovery in a PIPB column on cumene yield for a world class capacity cumene process is illustrated. The line 602 represents incremental cumene yield (left y-axis) versus fractional TIPB recovery (x-axis) and the line 604 represents incremental TIPB recovered (right y-axis) in tonne/yr versus fractional TIPB recovery (x-axis). As seen in FIG. 6, a 0.505% increase in cumene yield results from the 99.5% TIPB recovery provided by the present disclosure. For larger processes like a 270 KMTA capacity process, these incremental increases can mean the difference between a profitable and an unprofitable plant.

Thus, it has been found that operating a disclosed single column design at a low top pressure of approximately 3 psia can result in an increased recovery of both DIPB and TIPB by exploiting the pressure/temperature relationship of the bottoms (heavy) material. To make the increased recovery of DIPB and TIPB of the disclosed process economical, the heating medium used for reboiling the column is high pressure steam, which is typically available at about 600 psig and about 489° F. Using low cost high pressure steam as the heat source, the process-side bottoms temperature can be lowered to within a preferred range of from about 430-465° F., more preferred from about 445-455° F., which results in a favorable polyalkylate-to-heavies ratio in the bottoms stream.

Because heavies production is a function of the reaction section conditions, a corresponding amount of polyalkylate will be required to dilute the bottoms liquid down to the bubble point temperature versus pressure in order to utilize available reboiler heating sources Therefore, a polyalkylate column bottoms pressure reduction results in reducing polyalkylate yield loss via the bottoms stream. This reduction is achieved by minimizing condensing system and column internal pressure drop contributions, thereby enabling a low total pressure drop across the column As shown in far right column of Table 1 below, the reduction in system pressure drop and bottoms temperature, combined with optimization of feed and side draw locations, makes it possible to increase DIPB recovery from a typical 99.5% up to 99.95% (equivalent to an additional 0.12% in cumene yield) and TIPB recovery from zero up to 99% (equivalent to another 0 505% in cumene yield) without using a deeper vacuum system, a larger column or second column or a substantially hotter reboiling medium, all of which would add substantially to capital and operating expenses.

TABLE 1

| Internals Specification/Type Trans Alkylation Catalyst System Pressure/Temperature psia/° F. | Trays Current | Trays New | Packing New |
| --- | --- | --- | --- |
| Receiver | 2.5/210 | 2.5/210 | 2.5/209 |
| Top of Column | 3.0/233 | 3.0/234 | 3.0/231 |
| Bottom of Column | 8.0/430 | 8.0/484 | 5.0/449 |
| Reflux to Feed Ratio (R/F, molal) | 2.5 | 2.5 | 2.5 |

TABLE 1-continued

| TIPB recovery (to side draw), % | Nil | 99.5 | 99.5 |
| --- | --- | --- | --- |
| Column Diameter, ft | 6.8 | 5.5 | 6.0 |
| High Pressure Steam, $T_{sat}$, ° F. | 489 | 489 | 489 |

Optimization of the location of the polyalkylate side draw relative to the top of the column and feed point allows for increased recovery of both TIPB and DIPB, without need for a larger column As shown in second data column from the left in Table 2 below, an optimum side cut point appears to at the 13$^{th}$ theoretical stage, where 99% DIPB recovery and 99% TIPB recovery is assumed for the theoretical stage calculations shown in FIG. 4 with the reboiler and receiver included in the stage count

TABLE 2

| Design Basis Internals | Current Trayed | New Packed | New Packed | New Packed | New Packed |
| --- | --- | --- | --- | --- | --- |
| Receiver Pressure, psia | 2.5 | 2.5 | 2.5 | 2.5 | 2.5 |
| Bottom Pressure, psia | 7.7 | 5 | 5 | 5 | 5 |
| Temperature Bottom, ° F. | 480 | 449 | 450 | 450 | 453 |
| Number of Theoretical Stages | 42 | 42 | 42 | 42 | 32 |
| Side Cut Position (% Down) | 11 (26%) | 13 (31%) | 17 (40%) | 21(50%) | 16 (50%) |
| Feed (% Down) | 26 (62%) | 26 (62%) | 31 (74%) | 33 (79%) | 25 (78%) |
| Side Cut Heavies (wppm) for R/F = 2 molal | N/A | 90 | 270 | 380 | 860 |
| R/F (molal) for Side Cut Heavies = 1000 wppm | N/A | 1.32 | 1.39 | 1.40 | 1.68 |

As is currently practiced, an internal "stab-in" condenser 46 (e.g, a vertical U-tube bundle) can continue to be used with the techniques of this disclosure as shown in FIG. 1. Use of an internal stab-in condenser 46 results in a reduced column pressure drop, from a typical 5-7 psi down to 3 psi or less. As an alternative shown in FIGS. 2 and 3, a "contact condenser" system 60, 60*b* including a vessel section, open or with packing or similar vapor-liquid contacting device can be used. With a contact condenser 60, 60*b*, upward-flowing condensable vapors contact downward-flowing sub-cooled condensed liquid directed over the contacting device 65, 65*b* Such a system can have a low column pressure drop and can be mounted internally, in the column top as shown in FIG. 2, or externally in a separate vessel as shown in FIG. 3, which might have greater application the retrofitting of existing columns.

High efficiency, random packing may be used in the column, primarily above the feed tray, reducing the conventional column pressure drop from the typical 5-7 psi down to less than 3 psi for the disclosed processes and columns. To eliminate possible concern over fouling of internals in the lower part of the column (i.e., the hottest section, below the feed point) due to buildup of tars and polymeric materials, low pressure drop fractionation trays can be utilized in place of packing Increasing re-flux-to-feed ratio and/or the number separation stages between the top of the column and the polyalkylate side draw outlet 27, 27*a*, 27*b* or side draw recycle inlet 27', 27*a*', 27*b*' improves DIPB recovery from the overhead purge (drag) stream. However, both increased DIPB and TIPB recovery without need for a larger column can be achieved by lowering the side draw and feed tray locations relative to the top of the column, while maintaining similar feed-to-side draw relative locations (to maintain heavies rejection from the side draw) and the external reflux-to-feed ratio Another benefit of the lower column pressure, lower bottoms temperature and the location of the feed point 23, 23*a*, 23b is the potential to make use of an intermediate reboiler 37, 37a, 37b Intermediate reboiling, with its attendant capital and/or utility cost advantages, was not considered economically feasible for DIPB and TIPB recovery prior to this disclosure Intermediate reboiling, as shown in FIGS. 1-3, using a lower temperature heating medium is also possible due to the reduction in column pressure drop to the disclosed range of less than 3 psi By selection of the appropriate stage, it is possible to use steam at the medium pressure level (typically, 150-200 psig and 367-388° F., respectively) or realize exchanger cost savings by continuing to use high pressure steam.

While only certain embodiments have been set forth, alternatives and modifications will be apparent from the above description to those skilled in the art These and other alternatives are considered equivalents and within the spirit and scope of this disclosure and the appended claims

What is claimed is:

1. A process for separating diisopropylbenzene (DIPB) and triisopropylbenzene (TIPB) from a feed comprising DIPB, TIPB, and polyalkylate heavies, the process comprising:
    introducing the feed into a distillation column operating at a column top pressure of less than 5 psia, a column bottoms pressure of less than 3 psi above the column top pressure and a bottoms temperature ranging from about 435° F. to about 465° F.; and
    taking off a side draw comprising at least 99.8 wt % of the DIPB and at least 50 wt % of the TIPB present in the feed and a bottoms stream comprising at least 95 wt % of the heavies contained in the feed,
    wherein the side draw is taken off from the column at a side draw point, the DIPB, TIPB and heavies are introduced into the column at a feed point, the column having a number of theoretical stages X, wherein X is an integer that is greater than 40 and an uppermost stage is numbered 1 and a lowermost stage is numbered X, the side draw point being disposed at a stage integrally numbered from about 0.26·X to about 0.40·X from the uppermost stage and the feed point being disposed at a stage integrally numbered from about 0.31·X to about 0.62·X from the uppermost stage.

2. The process of claim 1 wherein the column operates at a bottoms pressure of about 2 psi above the column top pressure.

3. The process of claim 1 wherein the bottoms temperature ranges from about 445° F. to about 450° F.

4. The process of claim 1 wherein the side draw comprises at least 99.9 wt % of the DIPB contained in the feed.

5. The process of claim 1 wherein the side draw comprises at least 90 wt % of the TIPB contained in the feed.

6. The process of claim 1 wherein the process is conducted so as to produce a hydrocarbon vapor at a top of the column and the process further comprises condensing at least a portion of the hydrocarbon vapor produced at the top of the column with a condenser.

7. The process of claim 6 wherein the condenser is contained within the column.

8. The process of claim 7 further comprising
    converting at least some of the hydrocarbon vapor to hydrocarbon liquid, and
    taking off at least to some of the hydrocarbon liquid off the column as overhead drag prior to re-introducing another part of said hydrocarbon liquid into the column as reflux.

9. The process of claim 6 wherein the condenser is a contact condenser disposed in the top of the column, and the process further comprises
    converting at least some of the hydrocarbon vapor in the contact condenser to hydrocarbon liquid, and
    taking off at least to some of the hydrocarbon liquid off the column at a side draw point disposed below the contact condenser and
    passing at least some of hydrocarbon liquid taken off the column at the side draw point through a cooler prior to being re-introduced into the column through the contact condenser.

10. The process of claim 9 further comprising
    purging at least a portion of the hydrocarbon liquid as overhead drag prior to reaching the contact condenser, and
    recycling at least a portion of the hydrocarbon liquid to the column at a point below the contact condenser.

11. The process of claim 6 wherein the condensing is conducted in a contact condenser disposed outside of the column, process further comprising
    converting at least some of the hydrocarbon vapor to hydrocarbon liquid in the contact condenser,
    removing at least to some of the hydrocarbon liquid from the contact condenser and
    passing at least some of hydrocarbon liquid removed from the contact condenser through a cooler prior to reintroducing the cooled hydrocarbon liquid into the contact condenser.

12. The process of claim 11 further comprising
    purging a portion of the hydrocarbon liquid as overhead drag prior to being reintroduced into the contact condenser and
    recycling a portion of the hydrocarbon liquid to the column after passing the hydrocarbon liquid through the contact condenser.

13. The process of claim 6 wherein the condensing is conducted at a condenser top pressure and a condenser bottoms pressure that is less than about 0.5 psi above the condenser top pressure.

14. The process of claim 1 wherein the side draw is withdrawn from the distillation column at a side draw point,
    the process further comprising withdrawing a draw off from the distillation column at a draw off point below the side draw point, and at least a portion of the draw off is reboiled and then returned to the distillation column.

* * * * *